United States Patent [19]

Mecca

[11] 3,970,756

[45] July 20, 1976

[54] MEDICINAL OR COSMETIC COMPOSITION CONTAINING ALLANTOIN GLYCINATE

[75] Inventor: Sebastian B. Mecca, Abington, Pa.

[73] Assignee: Schuylkill Chemical Company, Philadelphia, Pa.

[22] Filed: Aug. 8, 1975

[21] Appl. No.: 603,194

Related U.S. Application Data

[62] Division of Ser. No. 552,315, Feb. 24, 1975, Pat. No. 3,927,021.

[52] U.S. Cl. ............................... 424/273; 424/65
[51] Int. Cl.² ...................................... A61K 31/415
[58] Field of Search .................. 424/65, 68, 69, 273

[56] References Cited
UNITED STATES PATENTS
3,927,021  12/1975  Mecca .............................. 424/273
FOREIGN PATENTS OR APPLICATIONS
28,796  9/1970  Japan ................................ 424/273

Primary Examiner—Dale R. Ore
Attorney, Agent, or Firm—Howson and Howson

[57] ABSTRACT

An allantoin glycine complex is disclosed as is an allantoin salt glycine complex. Medicinal and cosmetic compositions containing these complexes are also disclosed.

1 Claim, No Drawings

MEDICINAL OR COSMETIC COMPOSITION CONTAINING ALLANTOIN GLYCINATE

This is a division of application Ser. No. 552,315, filed Feb. 24, 1975 now U.S. Letters Patent No. 3,927,021 which issued on Dec. 16, 1975.

BACKGROUND OF THE INVENTION

Allantoin is known to possess soothing, keratolytic moisturizing and anti-irritant properties. Various aluminum salts of allantoin are described in U.S. Pat. No. 2,761,867. These compounds combine the soothing and healing properties of allantoin with the astringent properties of aluminum and have found use in a variety of external cosmetic compositions and internal medicaments. For example, cosmetic chemists have utilized allantoin and allantoin salts in formulating a variety of products such as deodorants, antiperspirants, astringent lotions, after-shave lotions, diaper creams and the like. An alcohol-soluble aluminum chlorhydroxy allantoin propylene glycol complex useful in the formulation of various cosmetic compositions is described in U.S. Pat. No. 3,632,596.

Glycine (aminoacetic acid) is an amino acid which may be formed by ammonolysis of chloroacetic acid (see Kirk-Othmer, *Encyclopedia of Chemical Technology*, 2nd Edition, Vol. 2, p. 350, Interscience, 1963). Glycine is a simple amino acid and has found use, for example, when reacted with an aluminum derivative of isopropyl alcohol as a gastric antacid (Kirk-Othmer, *Encyclopedia of Chemical Technology*, 2nd Edition, Vol. 2, p. 430, Interscience, 1963).

It is an object of this invention to provide novel complexes containing allantoin or aluminum salts of allantoin and glycine which are stable both in dry form and solutions and are not sensitive to heat and which may be utilized in a variety of cosmetic formulations for their beneficial effects.

DETAILED DESCRIPTION OF THE INVENTION

The present invention relates to novel complexed compounds of allantoin or aluminum salts of allantoin and glycine and, more particularly, to an allantoin glycine complex; an aluminum chlorhydroxy allantoinate glycine complex, and an aluminum hydroxy allantoinate glycine complex.

The novel complexes of the present invention may be depicted as having the formulas:

$[C_4H_5N_4O_3]_x \cdot [H_2NCH_2COOH]_y$ (allantoin glycine complex) $[Al_2(OH)ClC_4H_4N_4O_3]_x \cdot [H_2NCH_2COOH]_y$ (aluminum chlorhydroxy allantoinate glycine complex) and $[Al(OH)C_2H_4N_4O_3]_x \cdot [H_2NCH_2COOH]_y$ (aluminum hydroxy allantoinate glycine complex) wherein $x$ and $y$ are each about 1 and refer to the number of mols of each component. In the foregoing formulas, $C_4H_5N_4O_3$ represents allantoin and $H_2NCH_2COOH$ represents glycine.

The novel complexes are prepared by thoroughly mixing the allantoin or the appropriate aluminum salt of allantoin with glycine in a dry, finely-divided state. Hot water, e.g. boiling, distilled water, is then added to the mixture with constant trituration. The resultant mass is then dried to provide the desired complexes. Allantoin, aluminum salts of allantoin and glycine are available commercially and are used in this form in preparing the complexes described herein.

The relative proportions of allantoin or aluminum salts of allantoin and glycine utilized in forming the desired complexes may vary somewhat. Regardless of the proportions, however, the products are complex chemical compounds in which the components are chemically bound.

In the complexes of the present invention, the allantoin or aluminum salts of allantoin and the glycine are preferably combined in a mol ratio of about 1 to 1. Therefore, in the preferred embodiments of this invention allantoin and glycine are combined in a mol ratio of about 1 to 1 to form the allantoin glycine complex allantoin glycinate. Likewise, aluminum chlorhydroxy allantoinate and glycine are combined in a mol ratio of about 1 to 1 to form the aluminum chlorhydroxy allantoinate glycine complex while aluminum hydroxy allantoinate and glycine are combined in a mol ratio of about 1 to 1 to form the aluminum hydroxy allantoinate glycine complex. In addition to the foregoing, an aluminum chlorhydroxy allantoin propylene glycol complex (U.S. Pat. No. 3,632,596) may be combined with glycine in a mol ratio of about 1 to 1 to form the aluminum chlorhydroxy allantoin propylene glycol glycine complex.

It is not necessary to utilize special reaction conditions to form the desired complexes. The complexes may be formed by a procedure in which the allantoin or aluminum salts of allantoin are combined with glycine with small quantities of water to form a uniformly mixed damp mass. The damp mass is then dried at 160° to 180°F. until the product is dry and has a relatively constant weight. In another procedure, boiling water is added to a mixture of allantoin or aluminum salts of allantoin and glycine. The amount of boiling water used in the reaction is not critical so long as an amount is added sufficient to wet the intimate mixture of the reactants and form a slurry or solution of the reactants. After the reaction is complete, the water is preferably removed from the product to a level below about 1%, by weight, based on the weight of the complex. This may be accomplished by heating the complex at a temperature of from about 160° to about 180°F. until the product is dry and has a relatively constant weight. The dry complexes are powders. Any drying means including spray drying may be employed, and vacuum may be employed to assist drying.

The desired complexes may also be prepared in a solid state reaction in which allantoin or aluminum salts of allantoin are combined with glycine and thoroughly blended to form a uniform mixture. The mixture is then passed through a micronizer where the material is pulverized to an extremely fine size (generally less than 10 microns) and intimately admixed with the formation of the desired complex in a solid state reaction.

It has been found that the complexes produced as the result of the present invention are remarkably stable whether in solution or heated. While not wishing to be bound by any precise theory, it is thought that the amphoteric characteristics of allantoin are responsible for the remarkable stability of the complexed products.

The complexes produced through this invention have the combined attributes of allantoin or the aluminum salts of allantoin e.g. healing, soothing, keratolytic, moisturizing and astringent properties (in the case of aluminum salts), bacteriostatic properties (in the case of aluminum chlorhydroxy allantoinate salts) with the properties of glycine, e.g. buffering, moisturizing and conditioning properties. The complexes are thus useful in a myriad of topical preparations such as hypoallergenic deodorants, antiperspirants, diaper rash treatments, local skin anti-irritants and the like.

The complexes have been found to be especially useful in antiperspirant-deodorant products, especially antiperspirant-deodorant products formulated with aluminum salts such as aluminum sulfate, aluminum chloride and aluminum chlorhydroxide. Such products frequently cause staining, destruction or charring of wearing apparel which becomes impregnated with the aluminum salts through contact with those areas of the body where the antiperspirant-deodorant products have been applied. High temperatures encountered in laundering, ironing or pressing the apparel causes the impregnated aluminum salts to decompose forming their corresponding aluminum acids which cause the undesired staining and possible charring and destruction of the clothing.

Surprisingly, it has been found that formulating antiperspirant-deodorant products with the complexes of this invention eliminates the undesired staining and destruction of clothing. It is theorized that the heat encountered in laundering causes ammonia to be released from the glycine component of the complex. The ammonia neutralizes the acid produced through decomposition of the aluminum salt portion of the complex, thereby eliminating the destructive effects of the acid.

It has further been found that the glycine phase of the complex acts as a buffer for any free acid liberated through body heat or perspiration. The complex thus contributes "built-in" anti-staining and buffering action to antiperspirant-deodorant products. The built-in buffering action imparts anti-irritant and hypoallergenic properties to antiperspirant-deodorant products, especially those products containing the aluminum chlorhydroxy allantoinate glycine complex, thereby increasing the spectrum of persons who can utilize such products without adverse effects.

The following examples illustrate the properties of typical complexes of the present invention and suggested uses for these complexes. The examples are illustrative only and not intended to limit the scope of the invention.

EXAMPLE 1

68 g. of allantoin are thoroughly mixed with 32 g. of glycine. 5 to 10 cc. of distilled water are then added and the mixture is triturated until a uniform damp mass is formed. The resulting mixture is then dried for 1 to 2 hours at 160°F. to 180°F. to a dry powder. The product is an allantoin glycine complex having the formula $[C_4H_5N_4O_3]_x \cdot [H_2NCH_2COOH]_y$ where $x$ and $y$ are each about 1. A 1% aqueous solution of the complex has a pH of about 6 to about 7.5. The complex is soluble to the extent of 1.5 to 2% in water at 25°C. while the complex is soluble to the extent of 15 to 20% in boiling water. The complex may be formulated in pharmaceutically acceptable carriers at levels of from about 0.2 to about 2% by weight, based on the total weight of the product, to form an agent useful in moisturizing creams and lotions where it provides soothing and buffering properties for various dermatological conditions. A like complex is formed by suspending 68 g. of allantoin and 2 g. of glycine in 100 cc. of boiling, distilled water, followed by evaporating the reaction mixture to dryness by heating to a temperature of 160°F. to 180°F. under vacuum.

EXAMPLE 2

170 g. of aluminum chlorhydroxy allantoinate are thoroughly mixed with 32 g. of glycine. 2 to 5 cc. of distilled water are then added and the mixture is triturated until a uniform damp mass is formed. The resulting mixture is then dried for ¼ to ½ hour at 161° to 180°F. to a dry powder. The product is an aluminum chlorhydroxy allantoinate glycine complex having the formula:

$$[Al_2(OH)_5ClC_4H_4N_4O_3]_x \cdot [H_2NCH_2COOH]_y$$

where $x$ and $y$ are each about 1. A 1% aqueous solution of the complex has a pH of 4.5 to 6. The complex is soluble to the extent of 2 to 2.5% in water at 25°C. The complex may be formulated in pharmaceutically acceptable carriers at levels of from about 0.2 to about 3%, by weight based on the weight of the product, to form a hypoallergenic antiperspirant-deodorant. A like complex is formed by suspending 170 g. of allantoin and 32 g. of glycine in 150 cc. of boiling, distilled water, followed by evaporating the reaction mixture to dryness by heating to a temperature of 160° to 180°F. under vacuum. An antiperspirant-deodorant of the following formulation may be prepared with the aluminum chlorhydroxy allantoinate glycine complex:

|   |   | % W.W. |
|---|---|---|
| 1. | Cerasynt 1000D | 2 |
|   | Emulsynt 2400 | 6.25 |
|   | Solulan 24 | 1.5 |
|   | Ceraphyl 31 | 1.5 |
| 2. | Propylene Glycol | 3 |
|   | Distilled Water | 43.95 |
|   | Aluminum Chlorhydroxy Allantoinate Glycine Complex | 0.2 |
|   | Veegum | 1 |
| 3. | Aluminum Chlorhydroxy Glycinate | 20 |
|   | Distilled Water | 19 |
| 4. | Dermodor 4775 | 0.5 |

Prepare 2 by mixing Veegum in distilled water with rapid agitation for about 45 minutes, followed by addition of the propylene glycol and the aluminum chlorhydroxy allantoinate glycine complex; heat the mixture at 70°C. Combine the ingredients of 1 and heat to 70°C. Combine 1 and 2 with continuous agitation until the mixture cools to 45°C. Combine 3 with this mixture, mix well and add 4.

EXAMPLE 3

124 g. of aluminum dihydroxy allantoinate are thoroughly mixed with 32 g. of glycine. 10 to 15 cc. of distilled water are then added and the mixture is triturated until a uniform damp mass is formed. The resulting mixture is then dried for ½ to 1 hour at 160° to 180°F. to a dry powder. The product is an aluminum hydroxy allantoinate glycine complex having the formula:

$$[Al(OH)C_2H_4N_4O_3]_x \cdot [H_2NCH_2COOH]_y$$

where $x$ and $y$ are each about 1. A 1% aqueous suspension of the complex has a pH of 6.5 to 8. The complex is insoluble in water. The complex may be formulated in pharmaceutically acceptable carriers at levels of from about ½ to 5%, by weight, based on the weight of the product, to form diaper rash palliatives and cosmetic preparations. A like complex is formed by suspending 125 g. of allatoin and 32 g. of glycine in 150 cc. of boiling, distilled water, followed by evaporating the reaction mixture to dryness by heating to a temperature of 160° to 180°F. under vacuum.

EXAMPLE 4

206 g. of aluminum chlorhydroxy allantoin propylene glycol are thoroughly mixed with 32 g. of glycine. 2 to 5 cc. of distilled water are then added and the mixture is triturated until a uniform damp mass is formed. The resulting mixture is then dried for ¼ to ½ hour at 160°F. to 180°F. to a dry powder. The product is an allantoin chlorhydroxy propylene glycol glycine complex having the formula:

$$[[Al_2(OH)_3ClC_4H_4N_4O_3][C_3H_8O_2]]_x \cdot [H_2NCH_2COOH]_y$$

wherein $x$ and $y$ are each about 1. The complex is soluble to the extent of 1.5 to 3% in water at 25°C. The complex may be formulated in pharmaceutically acceptable carriers at levels of from about 0.5% to 2%, by weight, based on the weight of the product to form antiperspirant-deodorants. A like complex is formed by suspending 206 g. of aluminum chlorhydroxy allantoin propylene glycol and 32 g. of glycine in 50 cc. of boiling, distilled water, followed by evaporating the reaction mixture to dryness by heating to a temperature of 160° to 180°F. under vacuum.

Having thus described the invention, What is claimed is:

1. A medicinal or cosmetic composition useful for topical application comprising from about 0.2 to about 2%, by weight based on the weight of the composition, of allantoin glycinate of the formula $$[C_4H_5N_4O_3]_x \cdot [H_2NCH_2COOH]_y$$

where x and y are each about 1 and a medicinal or cosmetic acceptable carrier.

* * * * *